(12) United States Patent
Das et al.

(10) Patent No.: US 9,772,329 B2
(45) Date of Patent: Sep. 26, 2017

(54) PROTEIN DETECTION METHOD

(75) Inventors: Jagotamoy Das, Toronto (CA); Shana O. Kelley, Toronto (CA)

(73) Assignee: The Governing Council of the University of Toronto, Toronto, ON (CA)

( * ) Notice: Subject to any disclaimer, the term of this patent is extended or adjusted under 35 U.S.C. 154(b) by 691 days.

(21) Appl. No.: 13/978,372

(22) PCT Filed: Jan. 11, 2012

(86) PCT No.: PCT/US2012/020965
§ 371 (c)(1),
(2), (4) Date: Dec. 12, 2013

(87) PCT Pub. No.: WO2012/097081
PCT Pub. Date: Jul. 19, 2012

(65) Prior Publication Data
US 2014/0005068 A1    Jan. 2, 2014

Related U.S. Application Data

(60) Provisional application No. 61/431,786, filed on Jan. 11, 2011.

(51) Int. Cl.
*G01N 33/543* (2006.01)
*G01N 27/327* (2006.01)

(52) U.S. Cl.
CPC ..... *G01N 33/5438* (2013.01); *G01N 27/3277* (2013.01); *G01N 33/54353* (2013.01)

(58) Field of Classification Search
None
See application file for complete search history.

(56) References Cited

U.S. PATENT DOCUMENTS

| | | | |
|---|---|---|---|
| 8,058,155 B1 * | 11/2011 | Bhansali | B82Y 10/00 257/14 |
| 2006/0160100 A1 | 7/2006 | Gao et al. | |
| 2008/0081329 A1 | 4/2008 | Elliott et al. | |
| 2009/0061451 A1 | 3/2009 | Achim et al. | |
| 2009/0270266 A1 | 10/2009 | Kelley et al. | |
| 2009/0283425 A1 * | 11/2009 | Clark | A61B 5/04001 205/792 |

(Continued)

FOREIGN PATENT DOCUMENTS

| | | |
|---|---|---|
| JP | 2005164388 A | 6/2005 |
| WO | WO 2010-025547 | 3/2010 |

OTHER PUBLICATIONS

Ferreira A.A.P. et al.: Electrochemical and spectroscopic characterization of screen-printed gold-based electrodes modified with self-assembld monolayers and Tc85 protein, Journal of Elect. Chemistry, 634(2):111-122(2009).

(Continued)

*Primary Examiner* — Melanie Y Brown

(57) ABSTRACT

Described herein are systems and methods for detecting a target analyte in a sample with electrodes, comprising a linker and an antibody attached to the linker, and measuring an electrocatalytic signal changes generated by binding of an analyte in the sample to the antibody. Also disclosed herein are kits for electrochemical detection of protein analytes.

14 Claims, 5 Drawing Sheets

(56) References Cited

U.S. PATENT DOCUMENTS

| | | | |
|---|---|---|---|
| 2009/0288960 A1* | 11/2009 | Rubin | G01N 33/5438 205/777.5 |
| 2009/0308744 A1 | 12/2009 | Nam et al. | |
| 2010/0041077 A1 | 2/2010 | Nagy et al. | |
| 2012/0067742 A1* | 3/2012 | Lee | C07D 333/18 205/782 |
| 2012/0073987 A1* | 3/2012 | Kraatz | C12Q 1/004 205/782 |

OTHER PUBLICATIONS

Geng et al: "Self-assembled monolayers-based immunosensor for detection of *Escherichia coli* using electrochemical impedance specroscopy", Electrochimica ACTA, Elsevier Science Publ. 53(14):4663-4668(2008).

Shun-Qin Hu et al.: "Capacitive immunosensor for transferrin based on an o-aminobenzenthiol oligomer layer", Analytica Chimica Acta, 458:(2); 297-304 (2002).

Yang L. et al: "Interdigitated array Microelectrode-Based Electrochemical Impedance Immunosensor for detection of *Escherichia coli* 0157:H7", American Chemical Society 76(4):1107-1113 (2004).

International Search Report and Written Opinion of the International Searching Authority of Application No. PCT/US2012/020965,mailed Aug. 28, 2012.

Das et al. A Nanocatalyst-Based Assay for Proteins: DNA-Free Ultrasensitive Electrochemical Detection Using Catalytic Reduction of p-Nitrophenol by Gold-Nanoparticle Labels', Journal of the American Chemical Society, vol. 128, No. 50. pp. 10622-16023 (2006). See p. 16022-16023; Fig. 1.

Esteva FJ., et al., Clinical utility of serum HER2/neu in monitoring and prediction of progression-free survival in metastatic breat cancer patients treated with trastuzumab-based therapies. Breast Cancer Res. 7(4):R436-43 (2005).

Zeng G., et al., "Nanostructures and molecular foce bases of a highly sensitive capacitive immunosensor" Proteomics 5(17):4347-53 (2005).

\* cited by examiner

PROTEIN DETECTION METHOD

CROSS-REFERENCE TO RELATED APPLICATIONS

This application is a United States National Stage Application filing under 35 U.S.C. §371 of International Application No. PCT/US2012/020965, filed on Jan. 11, 2012, which claims the benefit of priority of U.S. Provisional Patent Application Ser. No. 61/431,786, filed Jan. 11, 2011, now expired, both of which are hereby incorporated by reference herein in their entireties.

BACKGROUND OF THE INVENTION

The development of platforms for the sensitive and straightforward measurement of protein levels in clinical samples is an important goal that will facilitate expanded use of protein biomarkers in disease diagnosis. In order to provide useful information, detection schemes must exhibit high levels of specificity, low limits of detection, and robust performance in biological fluids like blood and serum. Given the emergence of multi-protein signatures for cancer and other diseases, multiplexing is also a valuable feature. The inclusion of internal and external controls and calibrators—critical for the development of accurate diagnostic assays—also requires multiplexing.

A variety of high-performing protein detection platforms are under development, and many of the most specific and sensitive use micro- and nanomaterials in their sensing schemes. Barcoded nanoparticles, nanowire transistors, enzyme-labeled beads, and microfluidic immunoarrays used with electrochemical readout all show promise for the development of biomarker analyzers. Challenges remain, however, pertaining to the development of simple analysis systems that are cost-effective and robust enough for clinical use.

SUMMARY OF THE INVENTION

Provided herein are detection systems for electrochemically detecting a protein analyte. In one aspect, the detection systems comprise an electrode comprising a linker on its surface, wherein the linker is attached to an antibody or fragment thereof capable of binding a protein analyte; and a redox reporter.

In some embodiments of the systems provided herein, the linker comprises a functional group capable of direct or indirect coupling to the antibody or fragment thereof. In other embodiments, the linker comprises a functional amine group. In yet other embodiments, the linker comprises a functional carboxylic acid group. In further embodiments, the linker is cystamine, cysteamine, mercapto propionic acid or 4-aminothiophenol. In yet further embodiments, the linker is attached to the antibody or fragment thereof via a second linker. In some instances, the second linker is glutaraldehyde or formaldehyde. In additional embodiments, the linker is attached to multiple copies of an antibody or fragment thereof.

In some embodiments of the systems provided herein, the antibody or fragment thereof is selected from the group consisting of polyclonal antiserum, polyclonal antibody, monoclonal antibody, Fab fragment, Fab' fragment, F(ab')$_2$ fragment, Fv fragment, single chain antibody, CDR peptide and diabodies.

In some embodiments of the systems herein, the redox reporter is capable of generating an electrochemical signal with the electrode when a potential is applied. In other embodiments, the redox reporter generates a faradaic current. In yet other embodiments, the redox reporter is capable of interfacial electron transfer. In further embodiments, the redox reporter is ferricyanide/ferrocyanide or ferrocene. In yet further embodiments, the redox reporter is hexachloroiridate(IV)/hexachloroiridate(III).

In some embodiments of the systems provided herein, the electrode is a noble metal. In other embodiments, the electrode is carbon. In yet other embodiments, the electrode is indium tin oxide. In further embodiments, the electrode is gold, palladium or platinum.

In some embodiments of the systems provided herein, the electrode is a microelectrode. In certain embodiments of the systems provided herein, the electrode is a nanostructured microelectrode. In some embodiments, the electrode is less than about 500 microns. In other embodiments, the electrode is less than about 250 microns. In still other embodiments, the electrode is less than about 100 microns. In yet other embodiments, the electrode is about 5 to about 50 microns. In further embodiments, the electrode is less than about 10 microns. In additional embodiments, the electrode is on a microfabricated chip. In further embodiments are present a plurality of electrodes arrayed on a substrate.

In some embodiments of the systems provided herein, the protein analyte is a biomarker for a disease, disorder or condition. In some instances the biomarker is a cancer biomarker. In certain instances, the biomarker is selected from the group consisting of BRCA1, BRCA1, Her2/neu, alpha-feto protein, beta-2 microglobulin, bladder tumor antigen, cancer antigen 15-3, cancer antigen 19-9, human chorionic gonadotropin, cancer antigen 72-4, cancer antigen 125 (CA-125), calcitonin, carcinoembryonic antigen, EGFR, Estrogen receptors, Progesterone receptors, Monoclonal immunoglobulins, neuron-specific enolase, NMP22, thyroglobulin, progesterone receptors, prostate specific antigen (PSA), prostate-specific membrane antigen, prostatic acid phosphatase, S-100, and TA-90, or a portion, variation or fragment thereof. In further instances, the biomarker is a biomarker for *Staphylococcus* or *Streptococcus* bacterial infections.

Also provided herein are methods for electrochemical detection of a protein analyte. In one aspect, the methods comprise contacting an electrode comprising a linker on its surface, wherein the linker is attached to an antibody or fragment thereof capable of binding a protein analyte with a sample and a redox reporter; measuring an electrochemical signal generated by the antibody-labeled electrode and the redox reporter when a potential is applied; and comparing the electrochemical signal to a signal of a control sample comprising no protein analyte; wherein a change of the signal detected relative to a signal of a control sample comprising no protein analyte is indicative of the presence of the protein analyte in the sample.

In some embodiments of the methods provided herein, the linker comprises a functional group capable of direct or indirect coupling to the antibody or fragment thereof. In other embodiments, the linker comprises a functional amine group. In yet other embodiments, the linker comprises a functional carboxylic acid group. In further embodiments, the linker is cystamine, cysteamine, mercapto propionic acid or 4-aminothiophenol. In yet further embodiments, the linker is attached to the antibody or fragment thereof via a second linker. In some instances, the second linker is glutaraldehyde or formaldehyde. In additional embodiments, the linker is attached with multiple copies of an antibody or fragment thereof.

In some embodiments of the methods provided herein, the antibody or fragment thereof is selected from the group consisting of polyclonal antiserum, polyclonal antibody, monoclonal antibody, Fab fragment, Fab' fragment, F(ab')$_2$ fragment, Fv fragment, single chain antibody, CDR peptide and diabodies.

In some embodiments of the systems herein, the redox reporter generates a faradaic current. In other embodiments, the redox reporter is capable of interfacial electron transfer. In further embodiments, the redox reporter is ferricyanide/ferrocyanide or ferrocene. In yet further embodiments, the redox reporter is hexachloroiridate(IV)/hexachloroiridate (III).

In some embodiments of the methods provided herein, the electrode is a noble metal. In other embodiments, the electrode is carbon. In yet other embodiments, the electrode is indium tin oxide. In further embodiments, the electrode is gold, palladium or platinum.

In certain embodiments of the methods provided herein, the electrode is a nanostructured microelectrode. In other embodiments, the electrode is less than about 100 microns. In yet other embodiments, the electrode is about 5 to about 50 microns. In further embodiments, the electrode is less than about 10 microns. In additional embodiments, the electrode is on a microfabricated chip.

In some embodiments of the methods provided herein, the protein analyte is a biomarker for a disease, disorder or condition. In some instances the biomarker is a cancer biomarker. In certain instances, the biomarker is selected from the group consisting of BRCA1, BRCA1, Her2/neu, alpha-feto protein, beta-2 microglobulin, bladder tumor antigen, cancer antigen 15-3, cancer antigen 19-9, human chorionic gonadotropin, cancer antigen 72-4, cancer antigen 125 (CA-125), calcitonin, carcinoembryonic antigen, EGFR, Estrogen receptors, Progesterone receptors, Monoclonal immunoglobulins, neuron-specific enolase, NMP22, thyroglobulin, progesterone receptors, prostate specific antigen (PSA), prostate-specific membrane antigen, prostatic acid phosphatase, S-100, and TA-90, or a portion, variation or fragment thereof. In further instances, the biomarker is a biomarker for *Staphylococcus* or *Streptococcus* bacterial infections.

Also provided herein are methods for multiplexed electrochemical detection of a plurality of protein analytes. In one aspect, the methods comprise contacting a first electrode comprising a linker on its surface, wherein the linker is attached to a first antibody or fragment thereof capable of binding a protein analyte with a sample and a redox reporter; measuring a first electrochemical signal generated by the first antibody-labeled electrode and the redox reporter when a potential is applied; contacting a second electrode comprising a linker on its surface, wherein the linker is attached to a second antibody or fragment thereof capable of binding a protein analyte with a sample and a redox reporter; measuring a second electrochemical signal generated by the second antibody-labeled electrode and the redox reporter when a potential is applied; and comparing the first and second electrochemical signals to respective signals generated by the first and second antibody-labeled electrode in a control sample comprising no protein analyte; wherein a change of the first and second electrochemical signals detected relative to the respective signals of a control sample comprising no protein analyte is indicative of the presence of the protein analyte in the sample.

In some embodiments of the methods provided herein, the first and second electrode are both on a microfabricated chip.

In other embodiments, the first and second electrode are on different microfabricated chips.

In some embodiments of the methods provided herein, the second antibody-labeled electrode is a reference control to the first antibody-labeled electrode. In other embodiments, the second antibody-labeled electrode detects abundant serum protein.

Also provided herein are methods for monitoring progression or response in a subject having a cancer. In one aspect, the methods comprise obtaining a biological sample from the subject; contacting an electrode comprising a linker on its surface, wherein the linker is attached to an antibody or fragment thereof capable of binding a protein analyte with the sample and a redox reporter wherein the antibody or fragment thereof binds to a protein analyte; measuring an electrochemical signal generated by the antibody-labeled electrode and the redox reporter when a potential is applied; and comparing the electrochemical signal to a signal of a control sample comprising no protein analyte; wherein a change of the signal detected relative to a signal of a control sample comprising no protein analyte is indicative of the presence of the protein analyte in the sample.

In some embodiments of the methods provided herein, the protein analyte is a biomarker for a disease, disorder or condition. In some instances the biomarker is a cancer biomarker. In certain instances, the biomarker is selected from the group consisting of BRCA1, BRCA1, Her2/neu, alpha-feto protein, beta-2 microglobulin, bladder tumor antigen, cancer antigen 15-3, cancer antigen 19-9, human chorionic gonadotropin, cancer antigen 72-4, cancer antigen 125 (CA-125), calcitonin, carcinoembryonic antigen, EGFR, Estrogen receptors, Progesterone receptors, Monoclonal immunoglobulins, neuron-specific enolase, NMP22, thyroglobulin, progesterone receptors, prostate specific antigen (PSA), prostate-specific membrane antigen, prostatic acid phosphatase, S-100, and TA-90, or a portion, variation or fragment thereof. In further instances, the biomarker is a biomarker for *Staphylococcus* or *Streptococcus* bacterial infections.

Also provided herein are kits for electrochemical detection of a protein analyte. In one aspect, the kits comprise an electrode comprising a linker on its surface, wherein the linker is attached to an antibody or fragment thereof capable of binding a protein analyte; and a redox reporter capable of generating an electrochemical signal with the electrode when a potential is applied.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

I. Electrochemical Detection Systems and Methods

Figure 1:
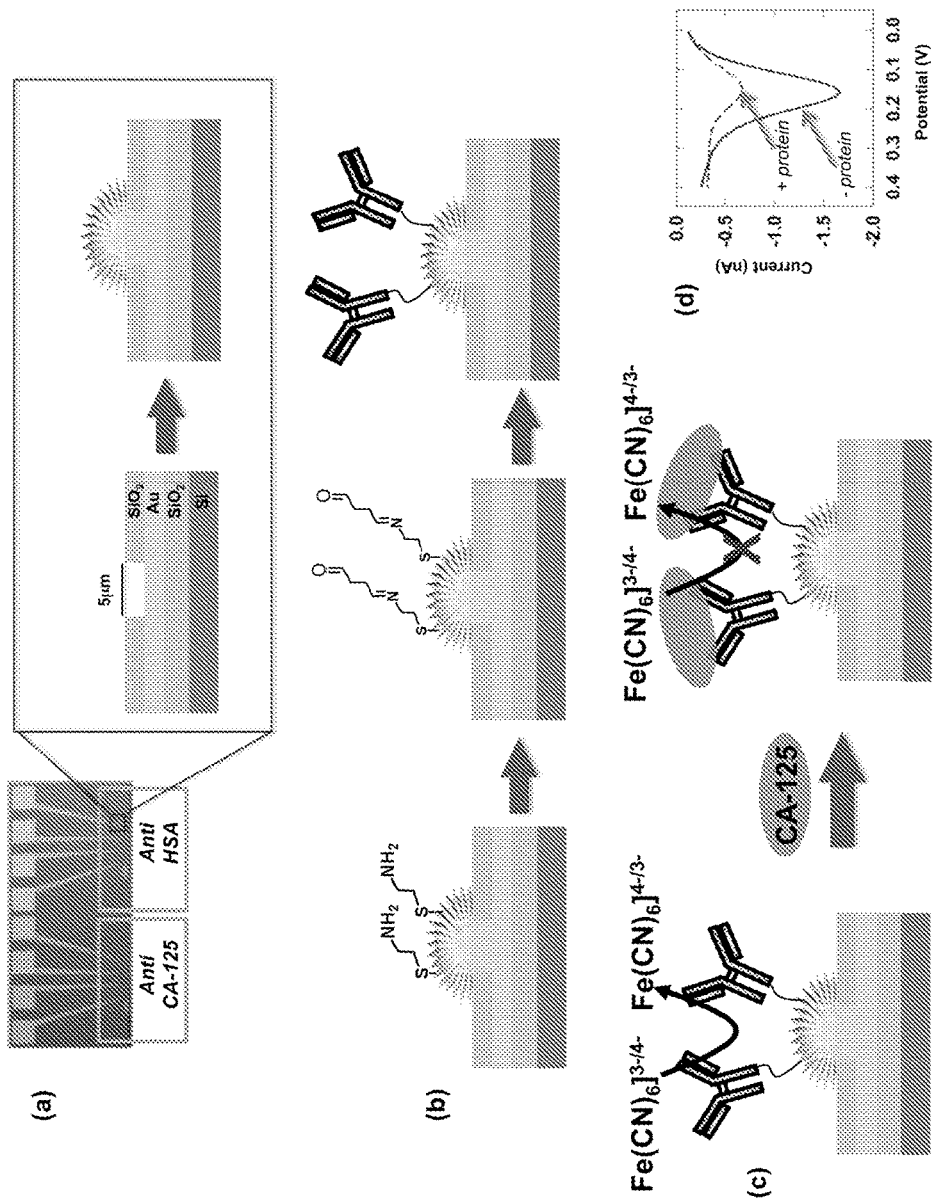
FIG. 1a. Photograph (left) of a multiplexed sensor chip showing microfabricated chip featuring 5 μm openings for the electrochemical deposition of electrodes and an illustration (middle) of aperture. A gold (Au) pattern is deposited on a silicon wafer using conventional photolithography and is then covered with a layer of $SiO_2$; 5 μm openings are then etched through this top layer to expose a circular section of Au. Schematic illustration of the generation of Au electrodes by Au electrodeposition (right).
FIG. 1b. Schematic of electrode functionalization; (left) a linker of cystamine is formed on Au structure; (middle) reaction with a bifunctional linker glutaraldehyde to introduce aldehyde groups at the sensor surface; (right) addition of the anti CA-125 antibody or anti Human Serum Albumin (HSA) antibody to prepare antibody-modified electrode sensors.
FIG. 1c. Schematic view of electrochemical detection for CA-125 antigen. The antigen-antibody binding hinders the interfacial electron transfer reaction of $[Fe(CN)_6]_{3-/4-}$.
FIG. 1d. Differential pulse voltammetry (DPV) showing the signal decrease observed after incubation of the CA-125 (10 U/ml in serum) for 40 min.

Provided herein are systems and methods for electrochemically detecting a target analyte in a sample. The presence of an analyte is detected by a change in an electrocatalytic signal. The use of such an electrical readout provides a method which is inexpensive, extremely sensitive, easy to miniaturize and easy to automate.

In one aspect of the detection systems and methods described herein, an electrode is provided wherein the electrode comprises a linker and wherein the linker is attached to an antibody or fragment thereof. The antibody or fragment thereof is capable of binding to a target analyte such as a protein. The electrode is in the presence of a redox reporter.

Redox reporters suitable for use in the systems and methods described herein are capable of generating an electrical signal (e.g., faradaic current) with the electrode when a potential is applied. Any redox reporter that generates a faradaic current or is capable of interfacial electron transfer with the electrode can be used. Non-limiting redox reporters, include but are not limited to small redox-active groups such as ferricyanide/ferrocyanide, ferrocene and hexachloroiridate(IV)/hexachloroiridate(III). The detection systems utilize redox reporters to generate baseline electrical signals with the electrode.

When a target analyte is present that binds to the antibody or fragment thereof, the electrical signal is attenuated. It is contemplated that attenuation of the signal is due to the target analyte blocking the redox reporter from effectively accessing the surface of the electrode. In other words, the antibody-analyte binding hinders interfacial electron transfer. See, by way of example only, FIG. 1c and 1d.

In one aspect, the signal changes corresponding to target analyte binding to the antibody are calculated as a percentage change in faradaic current:

$$\Delta I\% = \{(\text{mean } I_0) - (\text{mean } I_c)\}/\text{mean } I_0 \times 100$$

where mean $I_0$=mean current at zero target concentration, mean $I_c$=mean current at any concentration of target). In certain embodiments, the signal change is at least about 10%, at least about 15%, about 25%, about 30%, about 40%, about 50%, about 65%, about 75%, about 85%, about 90%, about 95%, about more than 100%, about twofold, about ten fold, about fifty fold, or greater. In certain instances, a change of the signal indicates that the analyte is bound to the antibody. With the change in the faradaic current, the detection systems and methods described herein are used in one aspect to determine the presence of a target analyte.

In another aspect, the detection systems and methods described herein are used to determine the concentration of a target analyte in a sample. In some embodiments, this is achieved via calibration of the detection system with known concentration standards of the target analyte. For example, a number of positive control samples, each with specific concentrations of analyte, are used to determine the percentage change in faradaic current for determination of an unknown quantity of an analyte in a test sample. The detection ranges for the detection systems and methods are dependent on the antibody, analyte and there binding capabilities as well as the redox reporter used. In some embodiments, the detection systems and methods described herein detect concentrations of analyte at about 500 femtomolar (fM) or about 100 pg/mL or lower.

In another aspect, the detection systems and methods described herein are multiplexed for detecting and/or determining the concentration of a plurality of target analytes. In some embodiments, multiplexed systems and methods comprise at least two electrodes, each comprising a linker with different antibodies attached to each linker. In certain instances, two, three, four, five, six, seven, eight, nine or ten electrodes, each comprising a linker with different antibodies attached to each linker are employed in a multiplexed system. In some embodiments, at least three, at least five, at least ten, at least fifteen, at least twenty, at least thirty, at least forty, or at least fifty or more electrodes are employed in a multiplexed system, each comprising a linker with different antibodies attached to each linker at each electrode. Alternatively, more than one electrode may contain the same antibody or antibody class; for example, duplicates of four electrodes, each group containing one of three separate antibodies, may be used in a twelve-electrode multiplexed system. Furthermore, an electrode may contain more than one antibody or antibody class; for example, on an individual electrode, more than one antibody, each recognizing a specific region of a protein or analyte, may be combined. In some instances, detection will occur only if a protein or analyte binds to all antibodies bound to the electrode. In some instances, detection will occur if a protein or analyte binds to at least one of the antibody groups bound to the electrode.

Multiplexing allows for a large variety of analytes to be detected simultaneously, thus creating an "analyte panel". Exemplary analyte panels can contain analytes related to a disorder, disease or condition, e.g., related biomarkers for a certain cancer. Multiplexing also allows for greater sensitivity for an analyte such as different antibodies that bind to the same target analyte via the same or different epitopes. The use of different antibodies, such as, for example, the use of a polyclonal and a monoclonal antibody that target the same analyte, allows the detection system to be more robust and sensitive than a single-plex system that uses only one type of antibody to detect an analyte. Multiplexing further allows internal calibration of the system to reduce false positives and negatives. For example, analysis of a target analyte can be performed in parallel with an analyte known to be stable such as an abundant serum protein.

In another aspect, the detection systems and methods described herein are employed to detect or diagnose a disorder, disease or condition or to monitor progression or response of a disorder, disease or condition. In some embodiments, a sample is obtained from a patient or subject and the detection systems and methods are used to detect the presence of and/or the concentration of a target analyte associated with the disorder, disease or condition. Exemplary disorders, diseases or conditions include cancers (e.g., breast, ovarian, prostate, pancreatic, colorectal, bladder and the like), infectious diseases (e.g., *Staphylococcus* or *Streptococcus* bacterial infections, MRSA, VISA, viral infections, fungal infections and the like), autoimmune diseases (e.g., Graves' disease, Lupus, arthritis, Goodpasture's syndrome and the like), metabolic disease and disorders (e.g., metabolic syndrome, insulin resistance, diabetes type I and II, Crohn's disease, irritable bowel syndrome and the like), HIV/AIDS, genetic diseases, and conditions associated with therapeutic drugs or toxicologic materials. Severity or stages of a disorder, disease or condition are determined in some embodiments by detecting the concentration of the target analyte where different concentrations indicate severity or stage. Likewise, in other embodiments, progression or response of a disorder, disease or condition are determined by detecting the concentration of the target analyte across various time points. Therapeutic effective of a pharmacological treatment, therapy or regimen can, in some embodiments, also be determined by detecting the concentration of the target analyte across various time points.

II. Electrodes

Electrodes for the detection systems and methods described herein are any electrically conductive materials with properties allowing linkers on the electrode's surfaces. Electrodes have the capability to transfer electrons to or from a redox reporter and are generally connected to an electronic control and detection device. In general, noble metals, such as, Ag, Au, Ir, Os, Pd, Pt, Rh, Ru and others in their family are suitable materials for electrodes. Noble metals have favorable properties including stability and resistance to oxidation, may be manipulated in various methods such as electrodeposition, and bind to thiols and disulfide containing molecules thereby allowing attachment of said molecules. Other materials can also be used, such as nitrogen-containing conductive compounds (e.g., WN, TiN, TaN) or silicon/silica-based materials, scuh as silane or siloxane. In certain embodiments, the electrode is gold, palladium or platinum. In other embodiments, the electrode is carbon. In further embodiments, the electrode is indium tin oxide.

In some embodiments, the electrode is a microelectrode. In other embodiments, the microelectrode is a nanostructured microelectrode ("NME"). NMEs are microelectrodes that feature nanostructured surfaces. Surface nanotexturing or nanostructures provide the electrode with an increased surface area, allowing for greater sensitivity, particularly in biosensing applications. Manufacturing of NMEs can be performed via electrodeposition. By varying parameters such as deposition time, deposition potential, supporting electrolyte type and metal ion sources, NMEs of a variety of sizes, morphologies and compositions may be generated. In certain instances, NMEs have a dendritic structure. Complexity of the dendritic structure is achieved by the varying the aforementioned electrodeposition parameters. Exemplary NMEs for use in the systems and methods described herein are described in International Pat. Appl. Ser. No. PCT/CA2009/001212 (published as WO/2010/025547) which is incorporated by reference in its entirety.

Other electrode structures can also be used in the detection systems and methods described herein, including, planar surfaces, wires, tubes, cones and particles. Commercially available macro- and micro-electrodes are also suitable for the embodiments described herein.

Electrodes are sized, for example, from between about 0.0001 to about 5000 microns in length or diameter; between about 0.0001 to about 2000 microns in length or diameter; from between about 0.001 to about 250 microns; from between about 0.01 to about 200 microns; from between about 0.1 to about 100 microns; from between about 1 to about 50 microns; from between about 10 to about 30 microns in length, or below about 10 microns in length or diameter. In certain embodiments, electrodes are sized at about 100 microns, about 30 microns, about 10 microns or about 5 microns in length or diameter. In further embodiments, electrodes are sized at about 8 microns.

In some embodiments, the detection systems and methods described herein, comprise one electrode for detection. In other embodiments, multiple electrodes are used. Use of multiple electrodes can be used in parallel to detect a target analyte via one antibody type attached to each electrode, in some embodiments. Alternatively, in other embodiments, multiple electrodes are used for multiplexing as described previously. Multiple electrodes can be configured in high or low density arrays. An exemplary 8 electrode array on a microfabricated chip for multiplexing use is depicted in FIG. 1a.

In further embodiments, an electrode is located upon a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like. Silica aerogels can also be used as substrates, and can be prepared by any known methods. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using well known techniques to provide for desired surface features, for example trenches, v-grooves, mesa structures, or the like. The substrate can take the form of a photodiode, an optoelectronic sensor such as an optoelectronic semiconductor chip or optoelectronic thin-film semiconductor, or a biochip. The location(s) of electrode(s) on the substrate can be addressable; this can be done in highly dense formats, and the location(s) can be microaddressable or nanoaddressable. In some embodiments, the electrode(s) is on a microfabricated chip.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials.

The substrate and/or its surface is generally resistant to, or is treated to resist, the conditions to which it is to be exposed in use, and can be optionally treated to remove any resistant material after exposure to such conditions.

III. Linkers

In one aspect, the electrode comprises a linker on the surface of the electrode. Linkers, in some embodiments, can be formed when linker molecules absorb and are organized into a molecular layer on a surface. Linkers suitable for use with the electrodes disclosed herein have a "head group" that strongly chemisorbs with metals (e.g., thiols and disulfides) and a tail with a functional group (e.g., —OH, —$NH_2$, —COOH, —CO, —$OCH_3$, —$NHNH_2$, -biotin, —NHS (amine-reactive N-hydroxysuccimide)). Examples of linkers include single chain or branched chain alkylthiols with a functional group. Other linker molecules include aromatic thiols such as thiophenol with a functional group. Suitable linker molecules include any molecule with a functional group that can directly or indirectly link to an antibody. Exemplary linker molecules include, but are not limited to, cystamine, cysteamine, mercapto propionic acid or 4-aminothiophenol. In some embodiments, the linker is cystamine.

Linkers are formed on the electrode surface when the electrode is immersed a solution of the linker molecule. Typical concentrations contain about 0.01 mM, 0.05 mM, 0.1 mM, 0.5 mM, 1 mM, about 2 mM, about 5 mM, about 10 mM, about 20 mM or about 50 mM or more of the linker molecule in an aqueous or ethanolic solution. The immersion is over a period of time ranging from a few hours to days. In some embodiments, the immersion is about 4 hours, about 8 hours, about 16 hours, about 24 hours, about 2 days, about 5 days or about 7 days. In some embodiments, the immersion is at room temperature. In other embodiments, the immersion is above room temperature. In further embodiments, the immersion is lower than room temperature.

Linkers can be attached directly or indirectly to an antibody by any known method. Direct attachment can, in some embodiments, be achieved through the functional groups of the linker molecules such as —CO functional groups that can react and attach to antibodies. Alternatively, a second linker or spacer can be conjugated onto the functional group by which the second linker or spacer can thereby attach to the antibody, in other embodiments. For example, linker molecules with —NH functional groups can react with a linker such as gluteraldehyde or formaldehyde which in turn can attach to antibodies. In further embodiments, the antibody can be derivatized so as to interact with functional group. For example, an avidin-labeled antibody can attach to a biotin functional group of a linker. These and other examples direct and indirect linkage are within the scope of the embodiments described herein.

IV. Antibodies

In one aspect, an antibody is used for determining the amount and/or concentration of a target analyte. Antibodies belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region. An antibody that is suitable for use in the present embodiments herein can be in any of a variety of forms, including, sera, a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present embodiments herein contemplate the use of any specificity of an antibody, polyclonal or monoclonal, and is not limited to antibodies that recognize and immunoreact with a specific antigen In some embodiments herein, in the context of both the therapeutic and screening methods, an antibody or fragment thereof is used that is immunospecific for a target analyte.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. See, e.g., U.S. Pat. No. 4,816,567; Morrison et al. Proc. Natl. Acad. Sci. 81, 6851 6855 (1984).

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Antibody fragments retain some ability to selectively bind with its antigen or receptor and are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) F(ab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$ $V_L$ dimer). It is in this configuration that the three CDRs of each variable domain interact to define an antigen binding site on the surface of the $V_H$ $V_L$ dimer Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds. Springer-Verlag, N.Y., pp. 269 315 (1994).

The term "diabodies" refers to a small antibody fragments with two antigen-binding sites, which fragments comprise a heavy chain variable domain (VH) connected to a light chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444 6448 (1993).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

The generation and preparation of antibodies is via any known method. See, for example, Green, et al., Production of Polyclonal Antisera, in: Immunochemical Protocols (Manson, ed.), pages 1 5 (Humana Press); Coligan, et al., Production of Polyclonal Antisera in Rabbits, Rats Mice and Hamsters, in: Current Protocols in Immunology, section 2.4.1 (1992), which are hereby incorporated by reference for the generation and preparation of polyclonal antibodies; Kohler & Milstein, Nature, 256:495 (1975); Coligan, et al., sections 2.5.1 2.6.7; and Harlow, et al., in: Antibodies: A Laboratory Manual, page 726 (Cold Spring Harbor Pub. (1988)), which are hereby incorporated by reference for the generation and preparation of monoclonal antibodies. Methods of generating antibody fragments can be generated similar to the protocols described in for example, Harlow and Lane, Antibodies: A Laboratory Manual, Cold Spring Harbor Laboratory, New York, (1988).

The antibodies are attached on the linker by any known method. The antibody can be attached directly to a selected functional group on the linker in some embodiments. Alternatively, the antibodies can be linked indirectly to the linker via a second linker or spacer in other embodiments.

V. Detectable Analytes/Biomarkers and Disease States/Uses

In one aspect, the target analyte is a protein. There are a large number of possible proteinaceous target analytes that may be detected using the present embodiments herein. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In some embodiments, the amino acids are in the (S) or L-configuration.

Suitable protein analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses (including orthomyxoviruses, (e.g., influenza virus), paramyxoviruses (e.g., respiratory syncytial virus, mumps virus, measles virus), adenoviruses, rhinoviruses, coronaviruses, reoviruses, togaviruses (e.g. m rubella virus), parvoviruses, poxviruses (e.g., variola virus, vaccinia virus), enteroviruses (e.g., poliovirus, coxsackievirus), hepatitis viruses (including A, B and C), herpesviruses (e.g., Herpes simplex virus, varicella-zoster virus, cytomegalovirus, Epstein-Barr virus), rotaviruses, Norwalk viruses, hantavirus, arenavirus, rhabdovirus (e.g., rabies virus), retroviruses (including HIV, HTLV-I and -II), papovaviruses (e.g., papillomavirus), polyomaviruses, and picornaviruses, and the like), and bacteria (including a wide variety of pathogenic and non-pathogenic prokaryotes of interest including *Bacillus*; *Vibrio*, e.g. *V. cholerae*; *Escherichia*, e.g. *Enterotoxigenic E. coli*, *Shigella*, e.g., *S. dysenteriae*; *Salmonella*, e.g., *S. typhi*, *Mycobacterium* e.g. *M. tuberculosis*, *M. leprae*; *Clostridium*, e.g. *C. botulinum*, *C. tetani*, *C. difficile*, *C. perfringens*; *Cornyebacterium*, e.g. *C. diphtheriae*; *Streptococcus*, *S. pyogenes*, *S. pneumoniae*, *Staphylococcus*, e.g., *S. aureus*; *Haemophilus*, e.g. *H. influenzae*; *Neisseria*, e.g. *N. meningitidis*, *N. gonorrhoeae*; *Yersinia*, e.g., *G. lamblia Y. pestis*, *Pseudomonas*, e.g. *P. aeruginosa*, *P. putida*; *Chlamydia*, e.g. *C. trachomatis*; *Bordetella*, e.g., *B. pertussis*; *Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β) human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone, testosterone; and (4) other proteins (including α-fetoprotein, carcinoembryonic antigen CEA).

In some embodiments, a protein analyte is a biomarker for a disease, disorder or condition. Exemplary biomarkers include, but are not limited to, (e.g., PSA, BRCA1, BRCA1, Her2/neu, AFP (α-feto protein), B2M (β-2 microglobulin), BTA (Bladder tumor antigen), CA 15-3 (Cancer antigen 15-3), CA 19-9 (Cancer antigen 19-9), hCG (Human chorionic gonadotropin), CA 72-4 (Cancer antigen 72-4), CA-125 (Cancer antigen 125), Calcitonin, CEA (Carcinoembryonic antigen), EGFR (Her-1), Estrogen receptors, Progesterone receptors, Monoclonal immunoglobulins, NSE (Neuron-specific enolase), NMP22, thyroglobulin, monoclonal immunoglobulins, NSE (Neuron-specific enolase), progesterone receptors PSA (Prostate specific antigen), total and free, prostate-specific membrane antigen (PSMA), prostatic acid phosphatase (PAP), S-100, and TA-90, or a portion or variation or fragment thereof. In certain instances, the biomarker is a biomarker for cancer. In other instances, the biomarker is a biomarker for bacterial infections. In further instances, the biomarker is a biomarker for *Staphylococcus* or *Streptococcus* bacterial infections.

VI. Samples

Samples for the detection systems and methods described herein can be any material suspected of containing an analyte. In some embodiments, the sample can be any source of biological material which comprises proteins that can be obtained from a living organism directly or indirectly, including cells, tissue or fluid, and the deposits left by that organism, including viruses, mycoplasma, and fossils. Typically, the sample is obtained as or dispersed in a predominantly aqueous medium. Nonlimiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant library comprising proteins, peptides, and the like.

The sample can be a positive control sample which is known to contain a target analyte. A negative control sample can also be used which, although not expected to contain the analyte, is suspected of containing it (via contamination of one or more of the reagents) or another component capable of producing a false positive, and is tested in order to confirm the lack of contamination by the target analyte of the reagents used in a given assay, as well as to determine whether a given set of assay conditions produces false positives (a positive signal even in the absence of target analyte in the sample).

The sample can be diluted, dissolved, suspended, extracted or otherwise treated to solubilize and/or purify any target analyte present or to render it accessible to reagents which are used in an amplification scheme or to detection reagents. Where the sample contains cells, the cells can be lysed or permeabilized to release the polynucleotides within the cells. One step permeabilization buffers can be used to lyse cells which allow further steps to be performed directly after lysis, for example a polymerase chain reaction.

VII. Devices for Use, Three Electrode Systems, Scanning Methods

Electron transfer is generally initiated electronically, with the application of at least a first electric potential applied to the system comprising the electrode and redox reporter. Precise control and variations in the applied potential can be via a potentiostat and either a three electrode system (one reference, one sample (or working) and one counter electrode) or a two electrode system (one sample and one counter electrode). In some embodiments, a potentiostat with a three electrode system is employed with a Ag/AgCl reference electrode and a platinum wire auxiliary electrode. Electrical signals can be measured either by cyclic voltammetry or differential pulse voltammetry. In certain instances, electrical signals are measured by cyclic voltammetry at a scan rate of about 50 m/v, of about 80 m/v, of about 100 m/v, of about 120 m/v, or of about 150 m/v. In other instances, electrical signals are measured by differential pulse voltammetry with a potential step of about 1-5 mV or about 2-10 mV, pulse amplitude of about 25-50 mV or about 40-75 mV, pulse about 25-50 ms or about 40-75 ms, and pulse period of about 10-100 ms or about 25-150 ms or about 50-200 ms.

In other instances, other means of detecting electrochemical potentials, including but not limited to potentiometric, amperometric, pulse voltammetry, cyclic voltammetry, broadband frequency response, impedance, or other electrochemical methods may be used to transduce output signals from the electrochemically modified electrodes of the systems and methods described herein.

VIII. Kits

Kits comprising components for the described systems and for performing the described methods are also provided. In some embodiments, a kit comprises one or more of the following components including an electrode, reagents to form a linker on the surface of the electrode, one or more antibodies and a redox reporter. The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for detection of one or more different target analytes.

EXAMPLES

Example 1

Preparation of Electrodes and Linkers

Chips are cleaned by sonication in acetone for 5 min, rinsed with isopropyl alcohol and DI water for 30 s, and dried with a flow of air. Electrodeposition is performed at room temperature; 5 µm apertures on the fabricated electrodes are used as the working electrode and are contacted using the exposed bond pads. Gold (Au) sensors are made using a deposition solution containing 20 mM solution of $HAuCl_4$ and 0.5 M HCl. The Au sensors are formed using DC potential amperometry at about 0-250 mV for about 100-300 s. Alternatively, Au structures may also be formed using chronopotentiometry, for example at about 15-40 nA for about 25-60 s.

Example 2

Coupling of Antibodies to Linkers

An aqueous solution containing 1-50 mM of 4-aminothiophenol or mercapto propionic acid is applied for 10-20 h at room temperature on AU sensors. The sensors are then washed with DI water 2-3 times for 2-4 minutes. The treated sensors were allowed to react at room temperature with 1.5-3.0% glutaraldehyde in water for 1 h followed by washing with DI water 2-3 times for 2-4 minutes. The functionalized sensors are then reacted with PBS containing 5-25 µg/ml antibody at room temperature for 1-2 h. The sensors are washed with PBS 2-3 times for 3-6 minutes. The unreacted aldehyde groups are blocked with PBS containing 1% (W/V) bovine serum albumin (BSA) for 1-2 hours at room temperature. The sensors are then washed 3-4 times with PBS for 4-7 minutes.

Example 3

Detection of Cancer Biomarker, CA-125

The development of platforms for the sensitive and straightforward measurement of protein levels in clinical samples is an important goal that will facilitate expanded use of protein biomarkers in disease diagnosis. In order to provide useful information, detection schemes must exhibit high levels of specificity, low limits of detection, and robust performance in biological fluids like blood and serum. Given the emergence of multi-protein signatures for cancer and other diseases, multiplexing is also a valuable feature. The inclusion of internal and external controls and calibrators also requires multiplexing.

CA-125 is an epithelial antigen that has been used as a marker for the detection of ovarian cancer. Several assays have been developed to detect CA-125, but most are not ideal either due to lack of sensitivity or the complexity of the detection procedure. The commercially available CA-125 immunoassay has a detection limit of 15 U/ml, which is sufficient to detect levels of CA-125 that correlate with the presence of disease (35 U/ml), but does not allow the relevance of significantly lower levels to be studied accurately.

The protein detection system disclosed herein was adapted to electrochemically detect a CA-125 cancer biomarker commonly present in ovarian cancers, via a microelectrode sensor on-a-chip design. The sensor chips allow for comparison of electrode sensors of different sizes, as well as determining a limit of detection exhibited down to 0.1 U/ml. The readout was performed in a single step involving the introduction of a non-covalently attached redox reporter group. The detection system reported exhibited was specific, with analysis of CA-125 in human serum. The multiplexing of the system allowed the analysis of the biomarker to be performed in parallel with an abundant serum protein, human serum albumin (HSA), for internal calibration.

Materials. CA-125 antigen and human serum from AB donors, anti human serum albumin (HSA) antibody, $HAuCl_4$ solution, potassium ferricyanide ($K_3[Fe(CN)_6]$), potassium ferrocyanide trihydrade ($K_2[Fe(CN)_6].3H_2O$), 50% (w/w) glutaraldehyde, and cystamine were purchased from Sigma-Aldrich. Anti CA-125 antibody was obtained from KalGene Pharmaceuticals Inc., Canada. ACS-grade acetone and isopropyl alcohol (IPA) were obtained from EMD (USA); 6 N hydrochloric acid was purchased from VWR (USA). Phosphate-buffered saline (PBS, pH 7.4, 1×) was obtained from Invitrogen. Human whole blood was obtained from Bioreclaimation (Westbury, N.Y.).

Chip & Electrode Fabrication: Chips were fabricated at the Canadian Photonics Fabrication Center. Briefly, three inch silicon wafers were passivated using a thick layer of thermally grown silicon dioxide. A 350 nm gold layer was deposited on the chip using electron-beam-assisted gold evaporation. The gold film was patterned using standard photolithography and a lift-off process. A 500 nm layer of insulating silicon dioxide was deposited using chemical vapor deposition; 5 µm apertures were imprinted on the electrodes using standard photolithography, and 2 mm×2 mm bond pads were exposed using standard photolithography. FIG. 1a depicts a photograph of an exemplary sensor chip (left) and representative layers (right).

Figure 2:
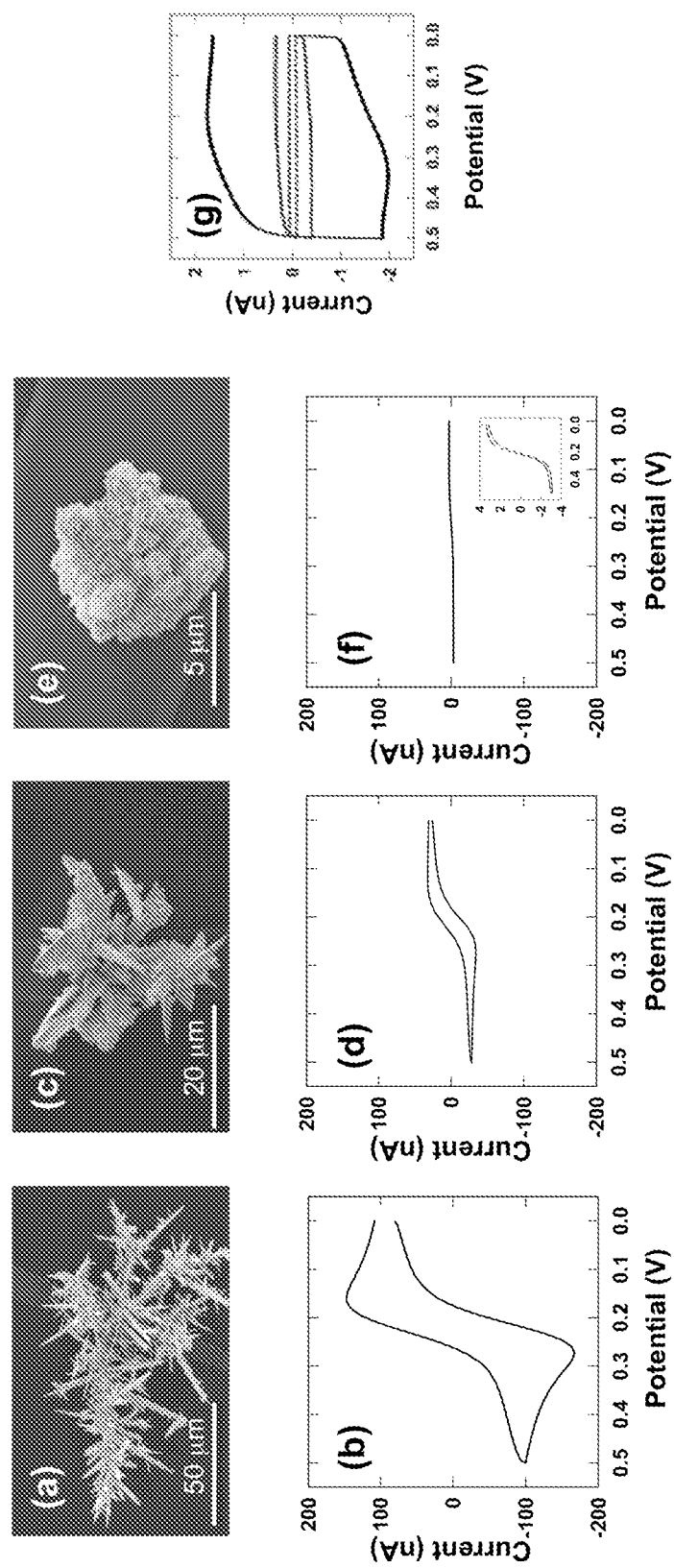
FIG. 2. SEM images and characteristic cyclic voltammograms of three differently-sized AU electrode sensors. SEM images of (a) 100 micron sensor. This structure was fabricated using DC potential amperometry at an applied potential of 0 mV for 200 s, (c) 30 micron sensor. This structure was fabricated using DC potential amperometry at an applied potential of 150 mV for 200 s, and (e) 8 micron sensor. This structure was fabricated using chronopotentiometry at an applied current of 30 nA for 50 s. Characteristic cyclic voltammograms of the three sensors were obtained in a 10 mM phosphate buffer solution containing 2.5 mM $[Fe(CN)_6]_{3-/4-}$ and 0.1 M KCl at a scan rate of 100 mV/s at sensors with size (b) 100 micron, (d) 30 micron, and (f) 8 micron sensors. Inset of FIG. 2(f) shows the magnified view of the cyclic voltammogram. (g) Capacitive current of three sensors reflecting surface area for each sensor size. Cyclic voltammograms were obtained in a 10 mM phosphate buffer solution containing 0.1 M KCl at a scan rate of 100 mV/s at sensors with size (outer curve) 100 micron, (middle curve) 30 micron, and (inner curve) 8 micron.

Chips were cleaned by sonication in acetone for 5 min, rinsed with isopropyl alcohol and DI water for 30 s, and dried with a flow of air. Electrodeposition was performed at room temperature; 5 μm apertures on the fabricated electrode sensors were used as the working electrode and were contacted using the exposed bond pads. Three different gold electrode sensors were made using a deposition solution containing 20 mM solution of $HAuCl_4$ and 0.5 M HCl using a process similar to the procedure as described in International Application Ser. No. PCT/CA2009/001212 (published as WO 2010/025547). The 100 micron and 30 micron gold electrode structures were formed using DC potential amperometry at 0 mV for 200 s and 150 mV for 200 s respectively; and 8 micron gold electrode structures were formed using chronopotentiometry at 30 nA for 50 s. FIGS. 2a, 2c and 2e depict SEM images of the 100 micron, 30 micron and 8 micron gold electrode structures respectively.

Determination of surface area of the sensors. The surface area of Au sensors was calculated by integrating the Au oxide reduction peak area obtained from cyclic voltammogram in the 50 mM $H_2SO_4$. In the forward scan, a monolayer of chemisorbed oxygen is formed and then it is reduced in the reverse scan. The reduction charge per microscopic unit area has been experimentally determined as 500 μC/geometric $cm^2$. The surface area was calculated by integrating the reduction peak (ca. 0.812 V vs. Ag/AgCl) to obtain the reduction charge, and dividing this by 500 μC/geometric $cm^2$.

Antibody Modification of the Electrodes: An aqueous solution containing 10 mM cystamine was applied for 16 h at room temperature on gold electrode sensors in order to form a uniform linker on the surface of the electrodes. Then, the electrodes were washed with DI water twice for 2 minutes. The linker was allowed to react at room temperature with 2.5% glutaraldehyde in water for 1 h followed by washing with DI water twice for 2 minutes. The functionalized electrodes were then reacted with PBS containing 10 μg/ml anti CA-125 antibody or anti Human Serum Albumin (HSA) antibody at room temperature for 1 h. The electrodes were washed with PBS twice for 5 minutes. The unreacted aldehyde groups were blocked with PBS containing 1% (W/V) bovine serum albumin (BSA). The electrodes were then washed three times with PBS for 5 min Solutions containing different concentrations of CA-125 in PBS or serum were applied to the antibody-modified electrode for 40 min at 37° C. The electrodes were washed with PBS prior to electrochemical readout.

Electrochemical Analysis and Scanning Electron Microscopy (SEM): Electrochemical experiments were carried out using a Bioanalytical Systems Epsilon potentiostat with a three-electrode system featuring a Ag/AgCl reference electrode and a platinum wire auxiliary electrode. Electrochemical signals were measured in a 10 mM phosphate buffer solution (pH 7) containing 2.5 mM $K_3[Fe(CN)_6]$, 2.5 mM $K_2[Fe(CN)_6]$, and 0.1 M KCl. Cyclic voltammetry (CV) was obtained with a scan rate of 100 mV/s and differential pulse voltammetry (DPV) signals were obtained with a potential step of 5 mV, pulse amplitude of 50 mV, pulse with 50 ms, and a pulse period of 100 ms. Signal changes corresponding to target protein binding to the antibody were calculated as follows: $\Delta I \% = \{(mean\ I_0) - (mean\ I_c)\}/mean\ I_0 \times 100$ (where mean $I_0$=mean current at zero target concentration, mean $I_c$=mean current at any concentration of target). The SEM images were obtained using a Hitachi S-3400 SEM.

Three different structures were fabricated on chips using different electrochemical methods and conditions. 100 micron (FIG. 2a), 30 micron (FIG. 2c), and 8 micron (FIG. 2e) sensors were generated by varying the electrodeposition conditions. The surface areas of the sensors were measured by scanning in sulfuric acid and measuring the amount of oxide formed and stripped from the surface, and areas of approximately $4 \times 10^{-6}$ $cm^2$ (8 micron sensor), $3 \times 10^{-5}$ $cm^2$ (30 micron sensor, and $1 \times 10^{-4}$ $cm^2$ (100 micron sensor) were obtained. The capacitive currents measured in buffer solution (FIG. 2g) were consistent with these values. Before testing the sensors for protein detection, cyclic voltammograms were obtained for each structure in a solution containing ferrocyanide and ferricyanide (FIG. 2b, 2d, and 2f). The 100 micron sensor displayed diffusion-limited currents and the 8 and 30 micron sensors exhibited plateau currents consistent with those expected for microelectrodes.

Figure 3:
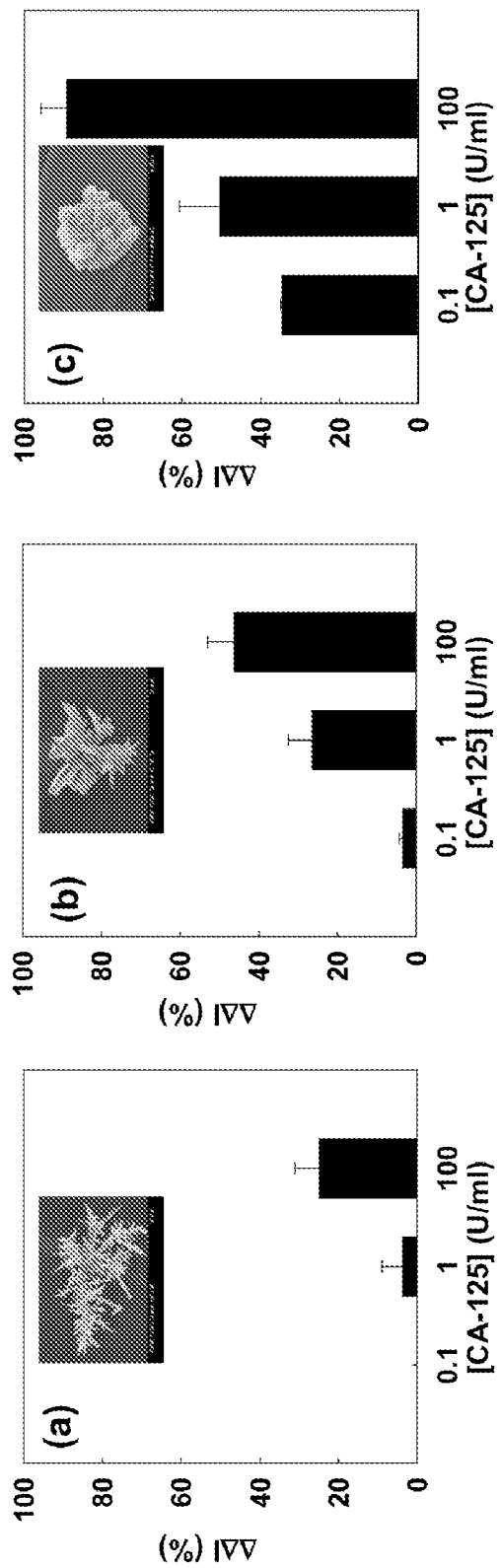
FIG. 3. Comparison of the sensitivities and detection limits of the immunosensors generated at three differently-sized Au structures. ΔA(1%) with concentration of CA-125 in PBS were obtained with (a) 100 micron sensor, (b) 30 micron sensor, and (c) 8 micron sensor.
Figure 4:
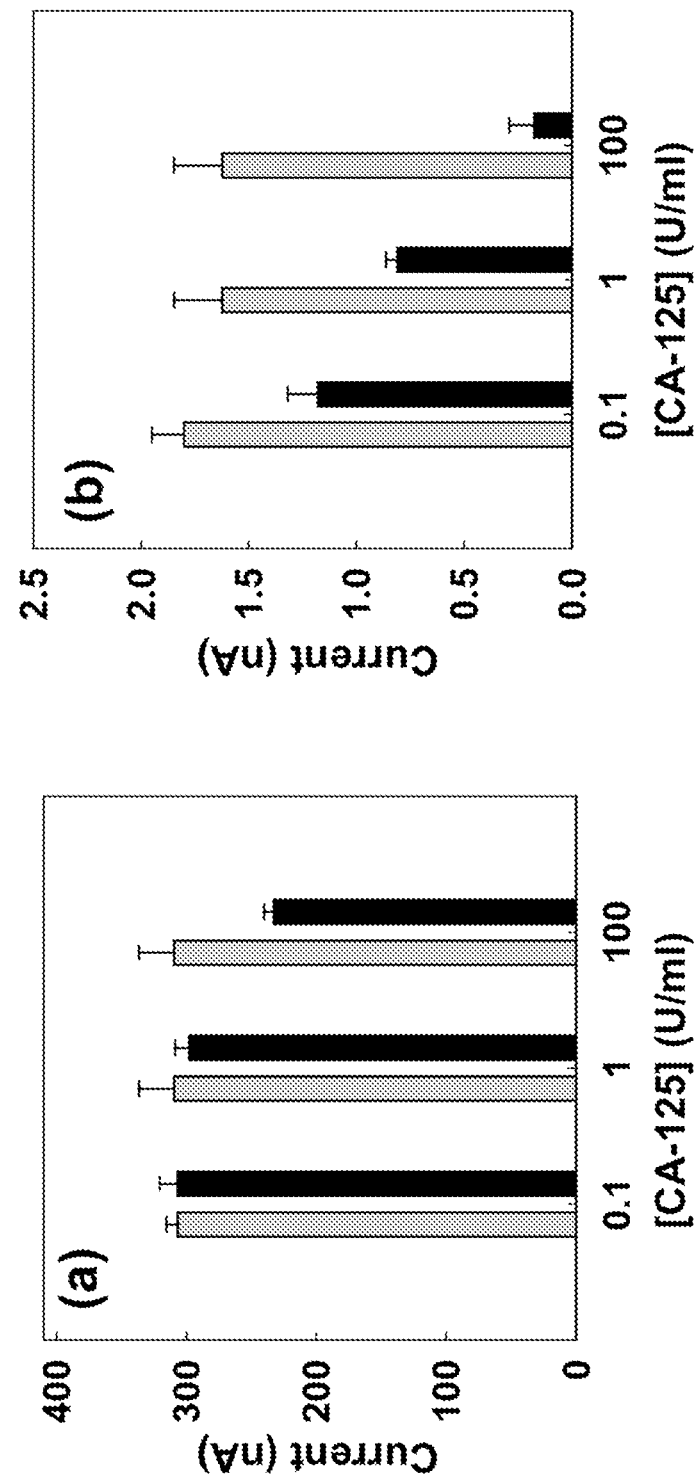
FIG. 4. Change of current of the sensors with size (a) 100 micron and (b) 8 micron before (grey bar) and after (black bar) incubation with different concentrations of CA-125 in PBS.

The detection limits of the immunosensors formed on the three differently-sized sensors were evaluated by measuring differential pulse voltammograms (DPVs) of $[Fe(CN)6]_{3-/4-}$ solutions before and after incubation with CA-125 for 40 minutes. With the largest sensors (FIG. 3a), concentrations of 10 U/ml were required for appreciable signal changes. With the intermediate 30 micron sensors, the detection limit approached 1 U/ml (FIG. 3b). With the smallest, 8 micron sensors, 0.1 U/ml of CA-125 was detectable (FIG. 3c). 0.1 U/ml of CA-125 antigen is equivalent to ~500 fM of CA-125 or 100 pg/ml.

Figure 5:
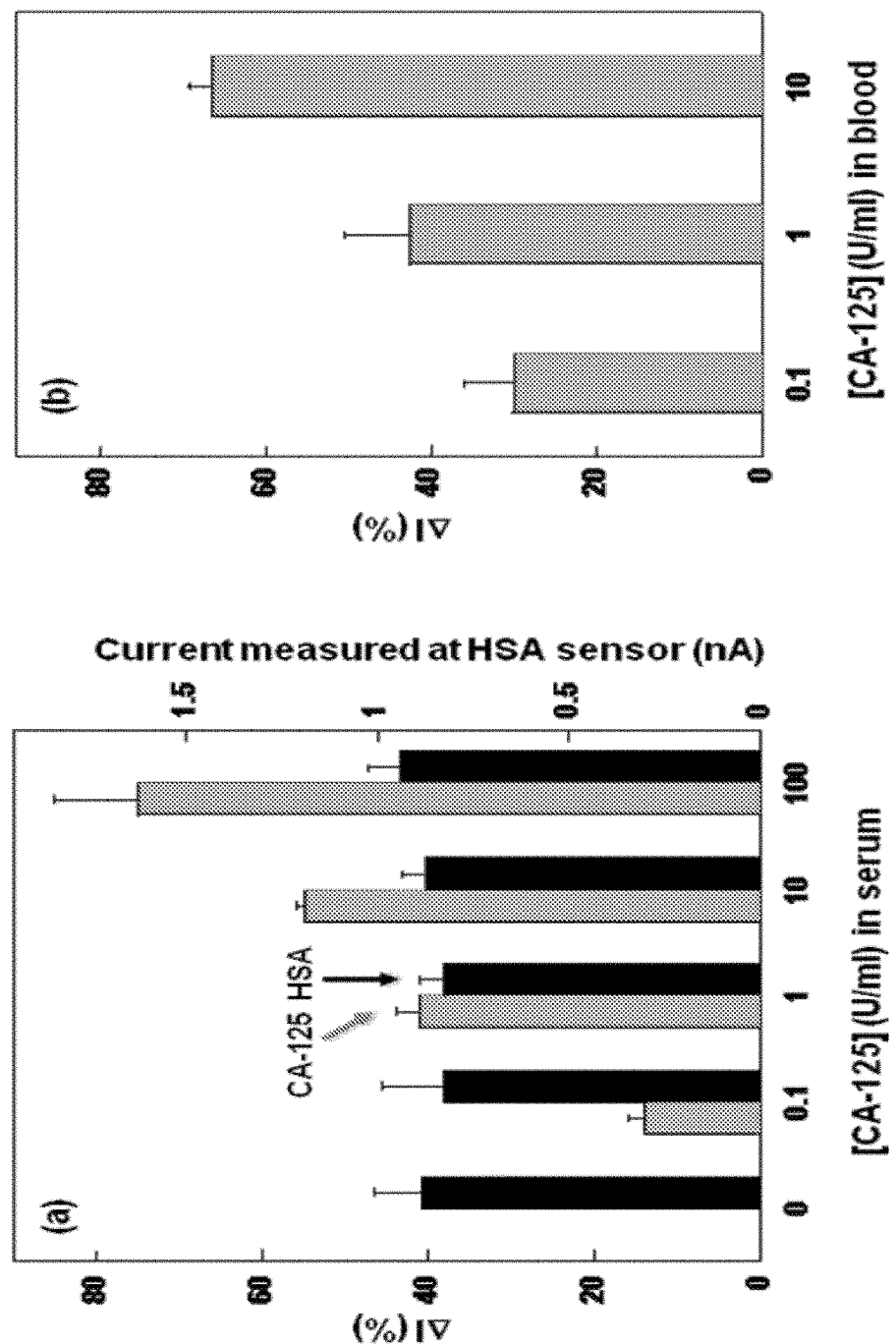
FIG. 5. Detection of CA-125 in serum and whole blood. (a) Simultaneous detection of CA-125 and HSA in spiked serum samples. Sample contained undiluted serum. Data obtained with serum only and serum spiked with different concentrations of CA-125. Grey bars indicate the data obtained with anti CA-125 antibody-modified immunosensors and black bars represent that for anti HSA antibody-modified immunosensors. Sensor size was 8 micron. (b) Detection of CA-125 in whole blood. Samples contained undiluted, unprocessed blood and the concentrations of CA-125 indicated.

To evaluate the exemplary detection system with biological fluids, detection of CA-125 samples in human serum was performed. Serum is a highly complex biological fluid containing large amounts of proteins and other molecules. Human serum albumin (HSA) was chosen as an internal standard due to constant and high concentrations of HSA in human sera. On a multiplex sensor chip, immunosensors for CA-125 and HSA were developed by forming layer of anti CA-125 antibody and anti HSA antibody respectively (FIG. 1a). Human serum spiked with different concentrations of CA-125 was applied to the multiplexed immunosensor and DPVs were recorded in a mixed solution of ferrocyanide and ferricyanide. FIG. 5a shows the $\Delta I \%$ (with respect to serum with 0 U/ml CA-125) values obtained for human serum spiked with different concentrations of CA-125. $\Delta I \%$ for sensors modified with anti CA-125 antibody increased with increasing concentrations of CA-125, whereas the $\Delta I \%$ for HSA was essentially constant for the immunosensors modified with anti-HSA antibody. The detection of CA-125 in parallel with a serum protein is a useful means to provide absolute measurements of the cancer biomarker.

The performance of this sensing system was also investigated in whole, unprocessed blood. Blood samples were spiked with CA-125 and the analysis was performed in the same manner as the serum and buffer studies. Interestingly, the same limit of detection was obtained, with 0.1 U/ml clearly resolved over background levels as depicted in FIG. 5b. This level of sensitivity achieved with an unprocessed blood sample indicates that this simple, straightforward electrochemical protein detection assay is also remarkably robust.

The following table depicts the approximate detection limit of CA-125 for various electrode sizes:

| Electrode diameter | Approximate limit of detection |
| --- | --- |
| 5 microns | 0.1 U/ml |
| 50 microns | 1 U/ml |
| 100 microns | 10 U/ml |
| 2000 microns (2 mm) | 100 U/ml |

REFERENCES

Rosi, N. L.; Mirkin, C. A. *Chem. Rev.* 2005, 105, 1547-1562.
Acharya, G.; Chang, C.-L.; Doorneweerd, D. D.; Vlashi, E.; Henne, W. A.; Hartmann, L. C.; Low, P. S.; Savran, C. A. *J. Am. Chem. Soc.* 2007, 129, 15824-15829.
Nam, J.-M.; Thaxton, C. S.; Mirkin, C. A. *Science* 2003, 301, 1884-1886.
Das, J.; Aziz, M. A.; Yang, H. *J. Am. Chem. Soc.* 2006, 128, 16022-16023.
Ho, J.-a. A.; Chang, H.-C.; Shih, N.-Y.; Wu, L.-C.; Chang, Y.-F.; Chen, C.-C.; Chou, C. *Anal. Chem.* 2010, 82, 5944-5950.
Fang, Z.; Kelley, S. O. *Anal. Chem.* 2009, 81, 612-617.
Pampalakis, G.; Kelley, S. O. *Analyst* 2009, 134, 447-449.
Roberts, M. A.; Kelley, S. O. *J. Am. Chem. Soc.* 2007, 129, 11356-11357.
Gasparac, R.; Taft, B. J.; Lapierre-Devlin, M. A.; Lazareck, A. D.; Xu, J. M.; Kelley, S. O. *J. Am. Chem. Soc.* 2004, 126, 12270-12271.
Lapierre-Devlin, M. A.; Asher, C. L.; Taft, B. J.; Gasparac, R.; Roberts, M. A.; Kelley, S. O, *Nano. Lett.* 2005, 5, 1051-1055.
Stoeva, S. I.; Lee, J.-S.; Smith, J. E.; Rosen, S. T.; Mirkin, C. A. *J. Am. Chem. Soc.* 2006, 128, 8378-8379.
Mcalpine, M. C.; Ahmad, H.; Wang, D.; Heath, J. R. *Nat. Mat.* 2007, 6, 379-384.
Gao, X. P. A.; Zheng, G.; Lieber, C. M. *Nano Lett.* 2010, 10, 547-552
Rissin, D. M.; Kan, C. W.; Campbell, T. G.; Howes, S.C.; Fournier, D. R.; Song, L.; Piech, T.; Patel, P. P.; Chang, L.; Rivnak, A. J.; Ferrell, E. P.; Randall, J. D.; Provuncher, G. K.; Walt, D. R.; Duffy, D.C. *Nat. Biotech.* 2010, 28, 595-600.
Rusling, J. F.; Sotzing, G.; Papadimitrakopoulos, F. *Bioelectrochemistry* 2009, 76, 189-194.
Gunawardana, C. G.; Kuk, C; Smith, C. R.; Batruch, I.; Soosaipillai, A.; Diamandis, E. P. *J. Proteome. Res.* 2009, 8, 4705-4713.
Sok, D.; Clarizia, L.-J. A.; Farris, L. R.; McDonald, M. J. *Anal. Bioanal. Chem.* 2009, 393, 1521-1523.
Kamp, G. J. V.; Verstraeten, A. A.; Kenemans, P. *Eur. J. Obstet. Gynecol. Reprod. Biol.* 1993, 49, 99-103.
Tang, D.; Yuan, R.; Chai, Y. *Anal. Chim. Acta* 2006, 564, 158-165.
He, Z.; Gao, N.; Jin, W. *Anal. Chim. Acta* 2003, 497, 75-81.
Mongia, S. K.; Rawlins, M. L; Owen, W. E.; Roberts, W. L. *Am. J. Clin. Pathol.* 2006, 125, 921-927
Mouffouk, F.; Chishti, Y.; Jin, Q.; Rosa, M. E.; Rivera, M; Dasa, S.; Chen, L. *Anal. Biochem.* 2008, 372, 140-147.
Chen, S.; Yuan, R.; Chai, Y.; Xu, Y.; Min, L; Li, Na. *Sens. Actuators B* 2008, 135, 236-244.
Wang, J.; Ren, J. *Electrophoresis* 2005, 26, 2402-2408.
Fu, X.-H. *Electroanalysis* 2007, 19, 1831-1839.
Tang, D.; Su, B.; Tang, J.; Ren, J.; Chen, G. *Anal. Chem.* 2010, 82, 1527-1534.
Wu, J.; Yan, Y.; Yan, F.; Xu, H. *Anal. Chem.* 2008, 80, 6072-6077.
Liu, H.; Fu, Z.; Yang, Z.; Yan, F.; Xu, H. *Anal. Chem.* 2008, 80, 5654-5659.
Soleymani, L.; Fang, Z.; Sargent, E. H.; Kelley, S. O, *Nat. Nanotech.* 2009, 4, 844-848.
Soleymani, L.; Fang, Z.; Sun, X.; Yang, H.; Taft, B. J.; Sargent, E. H.; Kelley, S. O. *Angew. Chem. Int. Ed.* 2009, 48, 8457-8460.
Yang, H.; Hui, A.; Pampalakis, G.; Soleymani, L.; Liu, F.-F.; Sargent, E. H.; Kelley, S. O. *Angew. Chem. Int. Ed.* 2009, 48, 8461-8464.
Fang, Z.; Soleymani, L.; Pampalakis, G.; Yoshimoto, M.; Squire, J. A.; Sargent, E. H.; Kelley, S. O. *Acs Nano* 2009, 3, 3207-3213.
Rand, D. A. J.; Woods, R. *J. Electroanal. Chem.* 1971, 31, 29.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for electrochemical detection of cancer antigen 125 (CA-125), comprising:
   providing a nanostructured microelectrode including a linker on its surface, the linker being attached to an antibody or fragment thereof capable of binding CA-125;
   contacting the nanostructured microelectrode with a sample including CA-125 and with a redox reporter, wherein binding of CA-125 to the antibody or fragment thereof hinders electron transfer between the redox reporter and the nanostructured microelectrode, the nanostructured microelectrode having a diameter of about 100 microns or less, the nanostructured microelectrode having a detection limit for CA-125 from about 0.1 U/ml to about 10 U/ml;
   applying a potential to the nanostructured microelectrode;
   measuring, in response to the applied potential, an electrochemical signal generated by the nanostructured microelectrode; and
   comparing the electrochemical signal to a control signal;
   deeming a change of the electrochemical signal detected relative to the control signal as indicative of the presence of CA-125 in the sample.

2. The method of claim 1, wherein the linker includes a functional group capable of direct or indirect coupling to the antibody or fragment thereof.

3. The method of claim 1, wherein the nanostructured microelectrode is labeled with multiple copies of the antibody or fragment thereof.

4. The method of claim 1, wherein the nanostructured microelectrode is capable of interfacial electron transfer.

5. The method of claim 1, wherein the measuring step includes employing a voltammetry-based approach.

6. The method of claim 1, wherein the nanostructured microelectrode is a first nanostructured microelectrode, the linker is a first linker, the antibody or fragment thereof is a first antibody or fragment thereof, the electrochemical signal is a first electrochemical signal, and the control signal is a first control signal, further comprising:
   providing a second nanostructured microelectrode including a second linker on its surface, the second linker being attached to a second antibody or fragment thereof;
   contacting the second nanostructured microelectrode with the sample and with the redox reporter, the second linker being attached to the second antibody or fragment thereof and capable of binding a protein analyte of the sample, the protein analyte being different than CA-125;

applying the potential to the second nanostructured microelectrode;

measuring, in response to the applied potential, a second electrochemical signal generated by the second nanostructured microelectrode; and comparing the second electrochemical signal to a second control signal;

deeming a change of the second electrochemical signal detected relative to the second control signal as indicative of the presence of the protein analyte in the sample.

7. The method of claim 6, wherein providing the first nanostructured electrode and providing the second nanostructured electrode includes providing a microfabricated chip having the first nanostructured electrode and the second nanostructured electrode fabricated thereon.

8. The method of claim 6, wherein the second nanostructured microelectrode is a reference control to the first nanostructured microelectrode.

9. A method for monitoring progression or response in a subject having cancer by electrochemical detection of cancer antigen 125 (CA-125) in a biological sample of the subject, comprising:

providing a nanostructured microelectrode including a linker on its surface, the linker being attached to an antibody or fragment thereof;

contacting the nanostructured microelectrode with the biological sample and with a redox reporter, wherein binding of CA-125 to the antibody or fragment thereof hinders electron transfer between the redox reporter and the nanostructured microelectrode, the nanostructured microelectrode having a diameter of about 100 microns or less, the nanostructured microelectrode having a detection limit for CA-125 from about 0.1 U/ml to about 10 U/ml;

applying a potential to the nanostructured microelectrode;

measuring in response to the applied potential, an electrochemical signal generated by the nanostructured microelectrode; and comparing the electrochemical signal to a control signal;

deeming a change of the electrochemical signal detected relative to the control signal as indicative of the presence of CA-125 in the biological sample.

10. The method of claim 1, wherein the deeming includes deeming a reduction in a signal magnitude of the electrochemical signal detected relative to the control signal as indicative of the presence of CA-125 in the sample.

11. The method of claim 9, wherein the deeming includes deeming a reduction in a signal magnitude of the electrochemical signal detected relative to the control signal as indicative of the presence of CA-125 in the sample.

12. The method of claim 6, wherein the first and second nanostructured microelectrode are on different microfabricated chips, wherein providing the first nanostructured electrode includes providing a first microfabricated chip having the first nanostructured electrode fabricated thereon, and wherein providing the second nanostructured electrode includes providing a second microfabricated chip having the second nanostructured electrode fabricated thereon.

13. The method of claim 6, wherein the second protein analyte includes abundant serum protein.

14. The method of claim 9, wherein the nanostructured microelectrode is less than about 10 microns in diameter and has a detection limit for CA-125 from about 0.1 U/ml to about 1 U/ml.

* * * * *